United States Patent
Sorensen et al.

(10) Patent No.: US 6,293,926 B1
(45) Date of Patent: Sep. 25, 2001

(54) PERISTALTIC PUMP AND CASSETTE

(75) Inventors: Gary P. Sorensen, Lake Forest; Tamer Akkas, Mission Viejo, both of CA (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/437,392

(22) Filed: Nov. 10, 1999

(51) Int. Cl.$^7$ .................................................... A61M 1/00
(52) U.S. Cl. ......................................... 604/153; 417/477.2
(58) Field of Search .................... 604/153, 4.01, 604/326, 5.01, 151, 152; 417/202, 477.2, 477.3, 477.4, 477.6, 477.7, 477.8; 494/51, 68, 69

(56) References Cited

U.S. PATENT DOCUMENTS

| | | |
|---|---|---|
| 4,140,118 | 2/1979 | Jassawalla . |
| 4,187,057 | 2/1980 | Xanthopoulos . |
| 4,479,761 | 10/1984 | Bilstad et al. . |
| 4,493,706 | 1/1985 | Borsanyi et al. . |
| 4,530,647 | 7/1985 | Uno . |
| 4,537,561 | 8/1985 | Xanthopoulos . |
| 4,713,051 | 12/1987 | Steppe et al. . |
| 4,758,238 | 7/1988 | Sundblom et al. . |
| 4,768,547 * | 9/1988 | Danby et al. . |
| 4,798,580 | 1/1989 | DeMeo et al. . |
| 4,838,865 | 6/1989 | Flank et al. . |
| 4,861,242 | 8/1989 | Finsterwald . |
| 4,921,477 | 5/1990 | Davis . |
| 4,923,375 | 5/1990 | Ejlersen et al. . |
| 4,935,005 | 6/1990 | Haines . |
| 4,963,131 | 10/1990 | Wortrich . |
| 5,041,096 | 8/1991 | Beuchat et al. . |
| 5,106,366 | 4/1992 | Steppe . |
| 5,195,960 | 3/1993 | Hossain et al. . |
| 5,207,647 | 5/1993 | Phelps . |
| 5,267,956 | 12/1993 | Beuchat . |
| 5,364,342 | 11/1994 | Beuchat et al. . |
| 5,403,277 | 4/1995 | Dodge et al. . |
| 5,429,602 | 7/1995 | Hauser . |
| 5,460,490 | 10/1995 | Carr et al. . |
| 5,470,312 | 11/1995 | Zanger et al. . |
| 5,518,378 | 5/1996 | Neftel et al. . |
| 5,588,815 | 12/1996 | Zaleski, II . |
| 5,709,539 | 1/1998 | Hammer et al. . |
| 5,746,708 * | 5/1998 | Giesler et al. ........................... 604/4 |
| 5,759,017 | 6/1998 | Patton et al. . |
| 5,897,524 * | 4/1999 | Wortrich et al. ....................... 604/30 |
| 5,906,598 * | 5/1999 | Giesler et al. ........................ 604/251 |
| 5,910,110 | 6/1999 | Bastable . |
| 5,927,956 * | 7/1999 | Lim et al. ........................ 417/477.13 |
| 5,996,634 * | 12/1999 | Dennehey et al. .................... 138/109 |
| 6,012,999 * | 1/2000 | Patterson ............................... 474/80 |
| 6,129,699 * | 10/2000 | Haight et al. ........................... 604/29 |

* cited by examiner

*Primary Examiner*—Richard K. Seidel
*Assistant Examiner*—Kevin C. Sirmons
(74) *Attorney, Agent, or Firm*—Jeffrey S. Schira

(57) ABSTRACT

A peristaltic pump having a molded flow channel contained on an elastomeric sheet that is bonded or mechanically attached to a rigid substrate. The pump head rollers are mounted radially from the axis of rotation of the pump motor and compress the elastomeric flow channels against the rigid substrate.

6 Claims, 2 Drawing Sheets

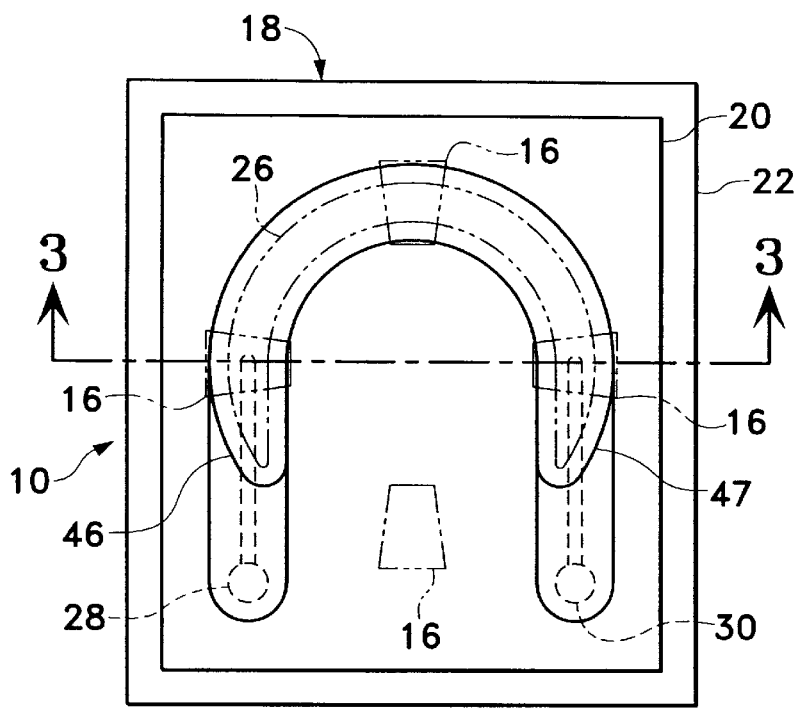
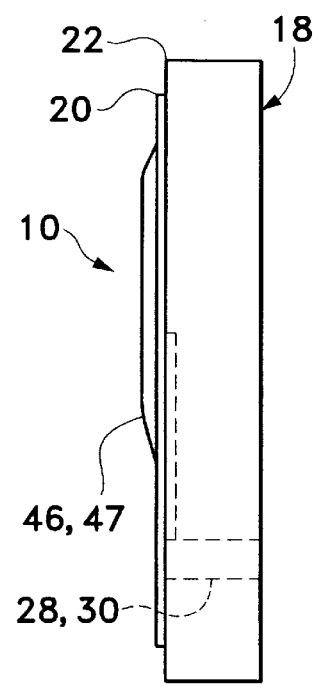
FIG. 1  FIG. 2
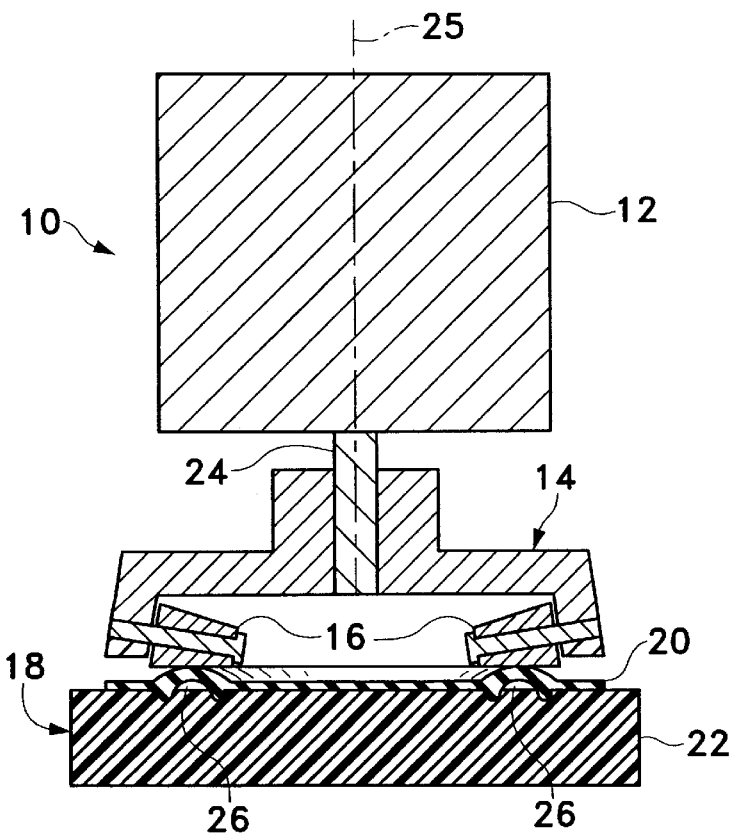
FIG. 3

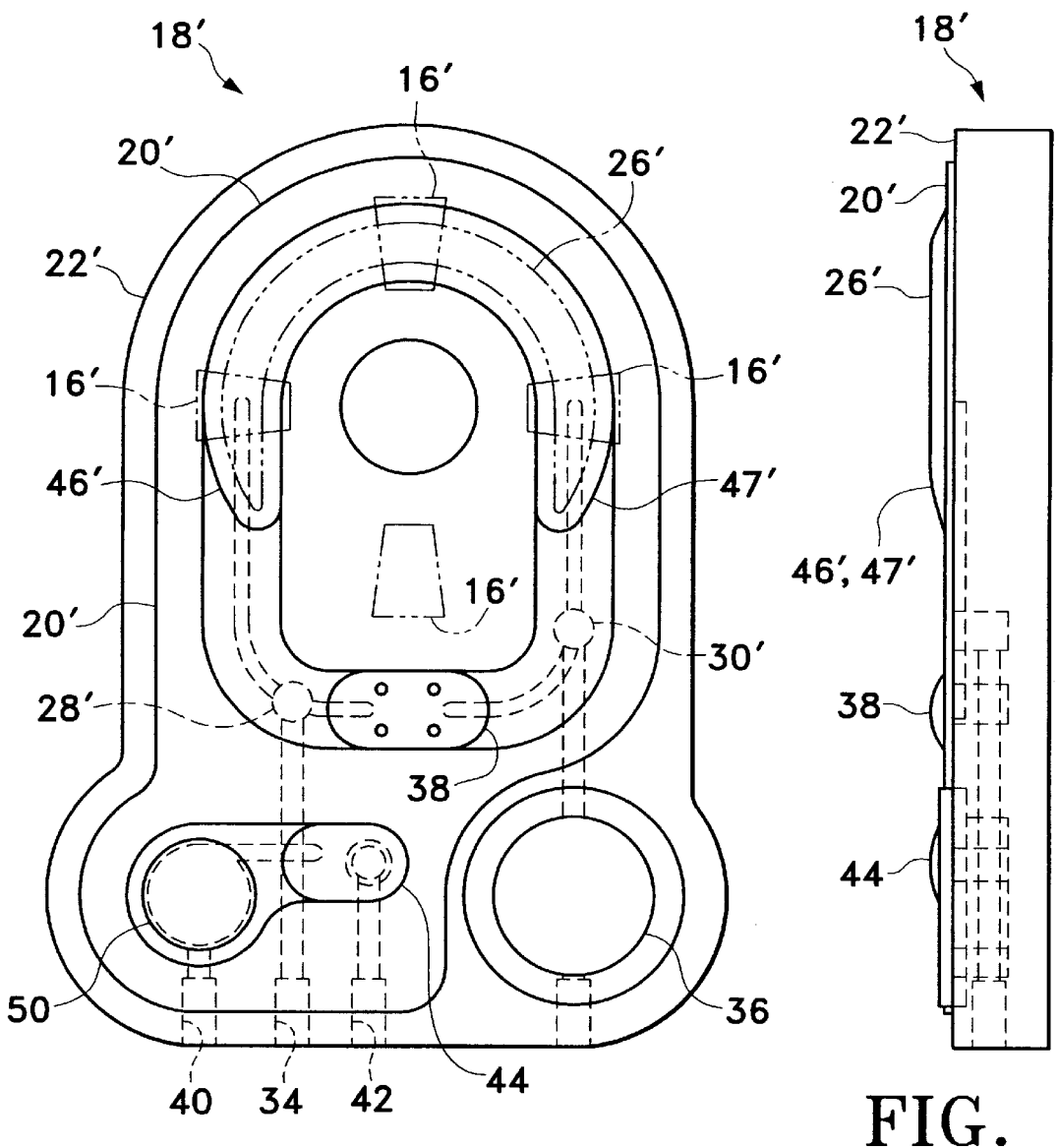
FIG. 4
FIG. 5
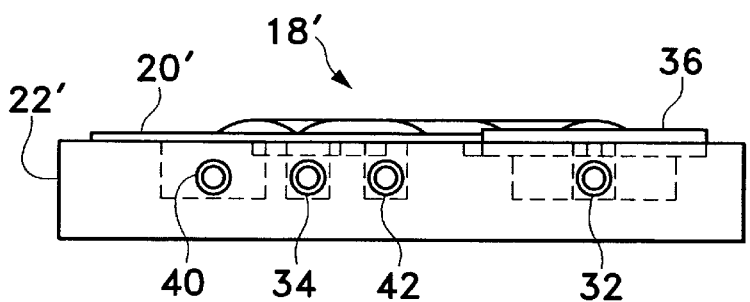
FIG. 6

PERISTALTIC PUMP AND CASSETTE

BACKGROUND OF THE INVENTION

The present invention relates generally to peristaltic pumps and more specifically to peristaltic pumps used in ophthalmic surgical equipment.

Most prior art peristaltic pumps work by compressing or squeezing a length of flexible tubing (sometimes between a fixed race) using a rotating roller head. As the roller head rotates, the rollers pinch off a portion of the tubing and push any fluid trapped in the tubing between the rollers in the direction of rotation. Peristaltic pumps are widely used in medical applications because of their predictable, constant flow properties. These prior art systems, however, typically require manual connection of the pump tube segment around the rotating roller head.

Prior art peristaltic pumps using rotating roller heads also typically impart unwanted pressure pulsations. Several pulsation damping devices have been developed to address this problem (see e.g., U.S. Pat. No. 4,921,477 (Davis)).

Accordingly, a need continues to exist for a peristaltic pump that reduces pressure pulsations and that is simpler and more economical to manufacture and use.

BRIEF SUMMARY OF THE INVENTION

The present invention improves upon prior art peristaltic pumps by providing a peristaltic pump having a molded flow channel contained on an elastomeric sheet that is bonded or mechanically attached to a rigid substrate. The pump head rollers are mounted radially from the axis of rotation of the pump motor and compress the elastomeric flow channels against the rigid substrate.

One objective of the present invention is to provide a peristaltic pump that uses molded elastomeric flow channels.

Another objective of the present invention is to provide a peristaltic pump having radially oriented pump rollers.

Yet another objective of the present invention is to provide a peristaltic pump having pump rollers that compress elastomeric flow channels against a rigid substrate.

These and other advantages and objectives of the present invention will become apparent from the detailed description, drawings and claims that follow.

BRIEF DESCRIPTION OF THE DRAWINGS

FIG. 1 is a schematic top plan view of a first embodiment of the present invention, with the motor and roller head removed for clarity.

FIG. 2 is a schematic side elevational view of a first embodiment of the present invention, with the motor and roller head removed for clarity.

FIG. 3 is a cross-sectional view of the first embodiment of the present invention taken at line 3—3 in FIG. 1.

FIG. 4 is a schematic top plan view of a second embodiment of the present invention, with the motor and roller head removed for clarity.

FIG. 5 is a schematic side elevational view of a second embodiment of the present invention, with the motor and roller head removed for clarity.

FIG. 6 is a schematic front elevational view of a second embodiment of the present invention, with the motor and roller head removed for clarity.

DETAILED DESCRIPTION OF THE INVENTION

As best seen in FIGS. 1, 2 and 3, in a first embodiment of the present invention, pump 10 of the present invention generally includes pump motor 12, roller head 14, containing one or more rollers 16 and cassette 18 having elastomeric sheet 20 applied to the exterior of relatively rigid body or substrate 22. Pump motor 12 preferably is a stepper or D.C. servo motor. Roller head 14 is attached to shaft 24 of motor 12 so that motor 12 rotates roller head 14 in a plane generally normal or perpendicular to axis 25 of shaft 24, and the longitudinal axes of rollers 16 are generally radial to the axis of shaft 24.

Sheet 20 contains molded fluid channel 26 that is generally planar, arcuate in shape (within the plane) and having a radius approximating that of rollers 16 about shaft 24. Fluid channel 26 fluidly connects ports 28 and 30. Sheet 20 may be made of any suitably flexible, easily molded material such as silicone rubber or thermoplastic elastomer. Sheet 20 is attached or bonded to substrate 22 by any suitable technique such as adhesive, heat fusion or mechanical crimping. Substrate 22 preferably is made of a material that is rigid with respect to sheet 20, such as a rigid thermoplastic, and may be made by any suitable method, such as machining or injection molding.

In use, cassette 18 is held in close proximity to roller head 14 so that rollers 16 compress channel 26 against substrate 22 as roller head 14 rotates. The longitudinal axes of the rollers are arranged so that roller 16 contact with channel 26 is generally parallel with the plane of channel 26. Such an arrangement eliminates the need to loop a length of flexible tubing over the pump roller head and thus simplifies the loading of pump channel 26 against pump roller head 14. Rollers 16 may be tapered along their axial length to accommodate the difference in path length traveled by the inner and outer sections of rollers 16 as roller head 14 rotates. Unwanted pressure pulsations could be minimized by providing channel transition regions 46 and 47 having internal cross-sections that taper from zero to the full cross-section of channel 26. These regions minimize the abrupt change in displaced volume as rollers 16 transition on or off of channel 26.

As best seen in FIGS. 4–6, in a second embodiment of the present invention, cassette 18' may contain additional fluid channels that provide control of irrigation fluid as well as aspiration fluid. For example, cassette 18' may contain aspiration inlet port 32 and aspiration outlet port 34 that are connected through channel 26'. Upstream of port 32, cassette 18' may contain pressure sensor 36, which may be any of a variety of non-invasive pressure sensors such as those disclosed in U.S. Pat. Nos. 5,910,110 (Bastable) and 5,470,312 (Zanger, et al.), the entire contents of which being incorporated herein by reference. Cassette 18' may also contain a vent pinch valve site 38 for allowing the venting of any vacuum from channel 26'. Irrigation fluid enters cassette 18' through port 40 and exits cassette 18' through port 42 and is controlled by valve or pinch valve site 44, which may be actuated by a plunger (not shown). Vent 38 may be operated in a similar method. In addition, between port 40 and irrigation pinch valve site 44, cassette 18' may contain irrigation pressure interface 50. Pressure interface 50 may be made from a thin molded membrane contained within elastomeric sheet 20' over a fluid chamber (not shown) contained within substrate 22'. Such an interface allows detection of irrigation pressure in a non-invasive manner using a surface contact pressure transducer or calibrated load cell.

This description is given for purposes of illustration and explanation. It will be apparent to those skilled in the relevant art that modifications may be made to the invention as herein described without departing from its scope or spirit.

What is claimed is:

1. A peristaltic pump, comprising:
   a) a pump roller head, the roller head attached to a rotating shaft and having one or more of rollers with longitudinal axes, the longitudinal axes of the rollers being generally normal or perpendicular to an axis of the shaft;
   b) a cassette having a body with an exterior;
   c) a sheet attached to the body, the sheet containing at least one molded fluid channel, the fluid channel being held in operative association with the rollers on the roller head.

2. The pump of claim 1 wherein the fluid channel is arcuate and lies on a plane and the longitudinal axes of the rollers are arranged so that roller contact with the fluid channel is generally parallel with the plane of the fluid channel.

3. The pump of claim 1 wherein the rollers are generally tapered along their axial length.

4. A peristaltic pump, comprising:
   a) a pump roller head, the roller head attached to a rotating shaft and having one or more of rollers with longitudinal axes, the longitudinal axes of the rollers being generally radial to an axis of the shaft;
   b) a cassette having a body with an exterior;
   c) a sheet attached to the body, the sheet containing at least one molded fluid channel, the fluid channel being held in operative association with the rollers on the roller head.

5. The pump of claim 4 wherein the fluid channel is arcuate and lies on a plane and the longitudinal axes of the rollers are arranged so that roller contact with the fluid channel is generally parallel with the plane of the fluid channel.

6. The pump of claim 1 wherein the rollers are generally tapered along their axial length.

* * * * *